(12) United States Patent
Zeller (10) Patent No.: US 11,540,741 B2
(45) Date of Patent: Jan. 3, 2023

(54) METHOD AND MEDICAL IMAGING APPARATUS FOR SUPPORTING A PREPARATION OF A PATIENT FOR A MEDICAL IMAGING INVESTIGATION

(71) Applicant: Siemens Healthcare GmbH, Erlangen (DE)

(72) Inventor: Mario Zeller, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 505 days.

(21) Appl. No.: 16/294,276

(22) Filed: Mar. 6, 2019

(65) Prior Publication Data

US 2019/0274582 A1 Sep. 12, 2019

(30) Foreign Application Priority Data

Mar. 6, 2018 (EP) .................................... 18160220

(51) Int. Cl.
| | |
|---|---|
| *A61B 5/055* | (2006.01) |
| *A61B 5/00* | (2006.01) |
| *A61B 5/107* | (2006.01) |
| *G01R 33/54* | (2006.01) |
| *G01R 33/28* | (2006.01) |
| *G16H 40/63* | (2018.01) |
| *A61B 6/04* | (2006.01) |
| *A61B 5/103* | (2006.01) |
| *A61B 90/00* | (2016.01) |
| *A61B 5/08* | (2006.01) |
| *A61B 5/318* | (2021.01) |

(52) U.S. Cl.
CPC ............ *A61B 5/055* (2013.01); *A61B 5/0046* (2013.01); *A61B 5/1079* (2013.01); *A61B 5/684* (2013.01); *A61B 5/704* (2013.01); *G01R 33/283* (2013.01); *G01R 33/543* (2013.01); *A61B 5/08* (2013.01); *A61B 5/1036* (2013.01); *A61B 5/318* (2021.01); *A61B 5/742* (2013.01); *A61B 6/0407* (2013.01); *A61B 2090/366* (2016.02); *G16H 40/63* (2018.01)

(58) Field of Classification Search
CPC ......................... A61B 2090/366; A61B 5/055
See application file for complete search history.

(56) References Cited

U.S. PATENT DOCUMENTS

| | | | | |
|---|---|---|---|---|
| 2002/0077533 | A1* | 6/2002 | Bieger | .................. A61B 34/20 600/300 |
| 2009/0251709 | A1* | 10/2009 | Kindlein | .............. A61N 5/1049 356/602 |
| 2011/0135190 | A1* | 6/2011 | Maad | .................. A61N 5/1049 382/154 |

(Continued)

*Primary Examiner* — Yi-Shan Yang
(74) *Attorney, Agent, or Firm* — Banner & Witcoff, Ltd.

(57) ABSTRACT

In a method and apparatus for supporting preparation of a patient for a medical imaging investigation, in particular a magnetic resonance investigation, patient data of a patient are acquired by operation of an acquisition unit. An item of position information of an object is calculated by a calculation computer, the calculation of the position information of the object taking place on the basis of the patient data and/or on the basis of an item of investigation information and/or on the basis of data from accessory units. The position information of the object is projected by means of a projection unit.

21 Claims, 3 Drawing Sheets

(56) References Cited

U.S. PATENT DOCUMENTS

| | | | |
|---|---|---|---|
| 2013/0083894 A1* | 4/2013 | Niebler | A61B 6/547 378/62 |
| 2013/0342350 A1* | 12/2013 | Popescu | A61B 5/055 340/573.1 |
| 2015/0272505 A1* | 10/2015 | Schmidt | A61B 5/055 600/407 |
| 2017/0328967 A1 | 11/2017 | Keil | |
| 2017/0343636 A1 | 11/2017 | Kroell | |
| 2019/0012944 A1* | 1/2019 | Hall | A61B 1/042 |
| 2020/0315711 A1* | 10/2020 | Richter | A61B 34/20 |

\* cited by examiner

METHOD AND MEDICAL IMAGING APPARATUS FOR SUPPORTING A PREPARATION OF A PATIENT FOR A MEDICAL IMAGING INVESTIGATION

BACKGROUND OF THE INVENTION

Field of the Invention

The present invention concerns a method for supporting the preparation of a patient for a medical imaging investigation. The present invention further concerns a medical imaging apparatus, and a non-transitory, computer-readable data storage medium encoded with programming instructions, designed to implement such a method.

Description of the Prior Art

A significant factor in the image quality in medical imaging investigations such as magnetic resonance investigations is an ideal or at least optimum positioning of possible accessory units, such as local radio-frequency antenna units, at the patient. The positioning of the accessory units is carried out by medical operating personnel so that the optimum positioning of the accessory units is often dependent upon the level of experience of the medical operating personnel. If the positioning of accessory units is carried out by inexperienced and/or unpracticed medical operating personnel, this can lead to problems in the positioning and thus also to problems in the image quality.

Methods for positioning are known from DE 10 2016 209 297 A1 and from DE 10 2016 208 018 A1.

SUMMARY OF THE INVENTION

An object of the present invention is to simplify the preparation of a patient for a medical imaging investigation, in particular a magnetic resonance investigation, for medical operating personnel.

The inventive method for supporting a preparation of a patient for a medical imaging investigation, in particular a magnetic resonance investigation, has the following steps.

Patient data of a patient are acquired by operation of an acquisition unit.

An item of position information of an object is calculated by a calculation computer, the calculation of the position information of the object taking place on the basis of the patient data and/or on the basis of an item of investigation information and/or on the basis of data from accessory units.

The position information of the object are projected by a projection unit.

Before the start of the medical imaging investigation, the patient to be investigated must first be prepared by medical operating personnel for this medical imaging investigation. The preparation of the patient includes, for example, positioning the patient on the patient positioning device. The positioning of the patient on the patient positioning device is also dependent upon the region of the patient that is to be investigated. For example, for a head investigation, the patient must be placed on the patient positioning device such that the patient is moved with his or her being moved first head into a patient receiving region of the medical imaging scanner. For a foot investigation and/or a knee investigation, however, the patient must be placed on the patient positioning device such that the patient is moved with the feet proceeding first into the patient receiving region of the medical imaging scanner.

Apart from the positioning of the patient, for preparation of the patient for the medical imaging investigation, when required, accessory units can also be applied at the patient. Such accessory units can be, for example, a local radio-frequency antenna unit for a magnetic resonance investigation on the patient. The accessory unit may also be an ECG unit and/or breathing sensors and/or other accessory units as are considered to be useful by those skilled in the art. These accessory units must be correctly positioned by the medical operating personnel, in particular with the correct orientation at the correct position on the patient.

The acquisition of the patient data preferably takes place autonomously and/or automatically using the acquisition unit. The acquisition unit can be arranged on the scanner of the medical imaging apparatus or on a wall or the room ceiling of an examination room in which the scanner of the medical imaging apparatus is situated. The acquisition unit has an acquisition region (field of view), the acquisition region encompasses the area in which the patient is being prepared for the medical imaging investigation. This acquisition region preferably is a region in front of the scanner unit of the medical imaging device, this region adjoining a front side of the scanner.

The patient data preferably designate the posture and/or the orientation and/or the extent, in particular the size and/or length and/or width and/or height of the patient. Alternatively or additionally, the patient data can also designate a position of the patient on the patient positioning device and/or in relation to the patient positioning device. The patient data can relate only to individual body areas or body regions of the patient, for example, dimensions of an arm or the head or the upper body, etc.

The acquired patient data are preferably transferred by a data transfer unit from the acquisition unit to the calculation computer. The calculation computer can actively call the acquired patient data from the acquisition unit. The data transfer between the calculation computer and the acquisition unit can take place hardwired or wirelessly.

Preferably, the calculation of the position information of the object by the calculation computer is carried out automatically and/or autonomously by the calculation computer. The calculation computer has a processor for this purpose. The calculation computer also includes calculation programs and/or calculation software that, when executed, cause the inventive method for supporting a preparation of a patient for a medical imaging investigation to be implemented. The calculation programs and/or calculation software can be stored in a memory of the calculation computer and/or of the medical imaging apparatus. In addition, the calculation programs and/or calculation software can also be deposited in an external memory store, for example a cloud, and the calculation computer accesses the calculation programs and/or calculation software via a data network. The calculation computer can be integrated within a control computer of the medical imaging apparatus. Alternatively or additionally, the calculation computer can be configured as an independent unit.

The investigation information designates, for example, an investigation region and/or an area of the patient to be investigated. The investigation region can already be stored in a patient database that the calculation computer can access. For example, the investigation region can already be acquired during a patient registration and stored in the patient database. It is also possible for the investigation region to be transmitted by the medical operating personnel during the preparation, for example by a manual entry of the investigation region as an input. The investigation information can also be, for example, a clinical picture of the patient, on the basis of which an investigation region is determined. The determination of the investigation region on the basis of a clinical picture can also take place automatically and/or autonomously by the calculation computer. For example, on the basis of a clinical picture "patient has headaches", the investigation region can initially be set to encompass the head of the patient.

The data of the accessory units is preferably stored within a database, and the calculation computer can access the data of the accessory units of the database via the database network. The data of the accessory units typically designate the geometry, in particular the length and/or the width and/or the height of the individual accessory units. Alternatively or additionally, the data of the accessory units can designate a target position of the individual accessory units in relation to the patient positioning device and/or in relation to the patient. In addition, the data of the individual accessory units can designate a usage area, in particular for which type of investigations the individual accessory units can be used.

The position information of the object can designate an item of position information of the patient. For example, the position of the patient needed for the pending medical imaging investigation can be stipulated and/or checked and/or corrected in relation to an accessory unit. In addition, the position information of the object can designate an item of position information of an accessory unit. For example, the position information can designate a target position of an accessory unit in relation to the patient and/or the patient positioning device.

The calculated position information of the object is preferably transferred by a data transfer unit from the calculation computer to the projection unit. The calculation computer can actively transfer and/or transmit the calculated position information of the object to the projection unit. The data transfer between the calculation computer and the projection unit can take hardwired or wirelessly.

As noted, the projection of the position information of the object takes place using a projection unit. The projection unit can be arranged on the scanner of the medical imaging apparatus or on a wall or the room ceiling of the examination room in which the scanner of the medical imaging apparatus is situated. Preferably, a projection region of the projection unit is directed to the patient and/or the patient positioning device during a preparation of the patient for the medical imaging investigation. This projection region preferably encompasses a region in front of the scanner of the medical imaging apparatus, this region adjoining a front side of the scanner unit. The projection of the position information of the object preferably takes place automatically or autonomously by the projection unit.

The present invention can be used for all medical imaging investigations considered useful by those skilled in the art, for example, a computed tomography investigation, a PET (positron emission tomography) investigation, etc. However, the present invention is particularly advantageously suitable for a magnetic resonance investigation, since local radio-frequency antenna units are always arranged on the patient in order to prepare the patient for the investigation.

The invention enables an advantageous support for medical operating personnel during a preparation of a patient for a medical imaging investigation. In this way, a simple and time-saving assistance for positioning the patient and/or for arranging and/or positioning accessory units can be provided for inexperienced and/or unpracticed medical operating personnel. Consequently, by the support for an optimized positioning of the patient and/or the accessory unit, a faulty positioning can be prevented and thus an image quality can advantageously be improved. Measurement repetitions due to faulty positioning thus can be prevented.

In an embodiment of the invention, the acquisition unit is a camera. The acquisition unit preferably is a 2-D camera or a 3-D camera. This serves as a particularly cost-effective acquisition unit for acquiring the patient data.

Alternatively or additionally, the acquisition unit can be or include a sensor that acquires the patient data. The sensor can be integrated within the patient positioning device and can be, for example, a pressure sensor and/or radio-frequency sensor integrated within the surface of the patient positioning device on which the patient lies, so that on the basis of a pressure distribution, a conclusion can be made regarding the posture and/or the orientation and/or the size and/or the position of the patient.

In another embodiment of the invention, it the patient data designates position data of the patient. The position data can represent the position of the patient on the patient positioning device. In addition, the position data can also represent a dimension of a standing patient. The position data can also represent a position of the region of the patient to be investigated. The position data can include both a position of the patient, in particular the region of the patient that is to be investigated, relative to a reference point and/or a reference position on the patient positioning device, as well as an extent of the patient, for example, the length and/or the size and/or the width and/or the height of the patient.

With this embodiment of the invention, an optimal position of the patient for the pending medical imaging investigation can be achieved. Additionally, a position of an accessory unit can be adapted to the position and/or to a physical extent of the patient. In this way, the medical operating personnel can obtain a patient-adapted or a patient-individual support for preparing the patient and thus a time-saving positioning of the patient and/or the accessory unit on the patient can be enabled.

In another embodiment of the invention, for the acquisition of the patient data, landmarks are arranged on the patient. This allows an unambiguous identification of individual body regions of the patient and/or of the region of the patient that is to be investigated can be performed by means of the acquisition unit and/or the calculation computer. In particular, an unambiguous orientation of the patient and/or of the region to be investigated can thereby be ascertained.

In another embodiment of the invention, the data of the accessory units are stored in a database. This embodiment of the invention enables a rapid and/or direct access to the data of the accessory units. In particular thereby, all the available accessory units for determining and/or calculating the position information of the object can be available in a simple manner to the calculation computer. The database can be integrated within the medical imaging device, for example, a memory of the medical imaging device. It is also possible for the database to be integrated into a central storage unit of an operator of the medical imaging device. Furthermore, the database can be formed by an external unit, for example, a cloud.

In another embodiment of the invention, a body model is determined on the basis of the acquired patient data. This allows the posture and/or the position of organs and/or further regions to be investigated, so anatomy such as joints, etc. can be rapidly and reliably determined or recognized. This also enables a simple determination of an optimum position of the organ and/or of the region of the patient that is to be investigated for the medical imaging investigation.

This enables a correct positioning of accessory units in relation to the region to be investigated, so that the image quality can be enhanced.

The body model is determined by the calculation computer wherein for this purpose, the calculation computer has a body model algorithm. The calculation and determination of the body model takes place on the basis of the acquired patient data.

In another embodiment of the invention, when calculating the position information of the object on the basis of the investigation information and/or on the basis of the patient data, at least one accessory unit is selected from a number of available accessory units. The correct selection of the accessory unit for the pending medical imaging investigation thus is simplified for unpracticed and/or inexperienced medical operating personnel. Preferably, the selection of the at least one accessory unit from the number of accessory units that are available is performed automatically and/or autonomously by the calculation computer.

For example, upon acquisition of a "feet first" position of the patient in which the patient is moved with the feet in front into the patient receiving region for the medical imaging investigation, initially only accessory units that are appropriate for foot investigations and/or leg investigations are selected, such as a foot radio-frequency antenna unit or a knee radio-frequency antenna unit. For example, upon acquisition of a "head first" position of the patient in which the patient is moved with the head in front into the patient receiving region for the medical imaging investigation, initially only accessory units that are appropriate for head investigations and/or chest investigations are selected, such as a head radio-frequency antenna unit and/or a chest radio-frequency antenna unit, etc. In addition, the selection of the accessory unit can be made on the basis of the patient's size. For example, a selection can be specified on the basis of the size of the body region of the patient to be investigated. Thus, for patients whose head circumference is so large that an available head recording region of individual head radio-frequency antenna units is too small to receive the head of the patient or the head together with headphones, a selection of a large head radio-frequency antenna unit can be displayed to the medical operating personnel. In addition, for small patients, a smaller body radio-frequency antenna unit can be selected than for large patients. Additionally, on the basis of the investigation information, the region to be investigated can be further specified so that a specific accessory unit can be selected. The investigation information can designate, for example, an investigation region and/or a region to be investigated and/or a clinical picture of the patient.

The multiple accessory units that are available preferably include all the accessory units available for medical imaging investigations on site that is at the location of the medical imaging device. The acquisition unit can also identify the individual accessory units, for example when the acquisition region of the acquisition unit is directed to a shelving unit that contains multiple accessory units. The projection unit can also, for example, illuminate (shine a light at) the selected accessory unit, so that a simple selection can be made by the medical operating personnel.

In another embodiment of the invention, the position information of the object designates a target position of the patient, the target position being projected onto the patient positioning device and/or the patient. The target position of the patient preferably represents an ideal position of the patient for the pending medical imaging investigation, i.e., the patient is to assume this target position for the medical imaging investigation in order to obtain a high image quality in the acquired image data.

The target position of the patient sets an optimum orientation of the region to be investigated in relation to the patient positioning device and/or in relation to accessory units, for example a head radio-frequency antenna unit and/or a knee radio-frequency antenna unit. Such accessory units can assume a pre-determined position in relation to the patient positioning device, so that the positioning of the patient must be adapted to this position.

Alternatively or additionally, the position information can also designate a change of position of the patient, which is projected onto the patient positioning device and/or the patient. A change of position can be determined by the calculation computer on the basis of a deviation of the target position of the patient from a current position of the patient, with the current position of the patient being determined on the basis of the acquired patient data. The change of position can be indicated, for example, by arrows that are projected onto the patient and/or the patient positioning device. With the arrows, an indication is given to the medical operating personnel as to the direction in which the patient is to be displaced. In addition, the change of position can take place by a projection of a contour of the patient at the desired target position. It may be the cast that only individual body parts and/or a body region of the patient is affected by the change of position. Thus, for example, in a liver investigation of a patient, the arms of the patient should not lie too close to the patient, in order to prevent artifacts in the image data of the liver. Such a target position of the arms of the patient can be projected by the projection unit onto the patient positioning device.

In another embodiment of the invention, the position information designates a target position of the accessory unit, said target position being projected onto the patient. This enables a particularly simple and time-saving application and/or positioning of the accessory unit, even for unpracticed and/or inexperienced medical operating personnel, such as when a radio-frequency antenna unit with a pilot tone transmitter should be positioned so that the pilot tone transmitter is arranged as close as possible to the heart of the patient. The target position of the pilot tone transmitter can be projected onto the patient for simple positioning of the corresponding radio-frequency antenna unit.

In another embodiment of the invention, following the projection of the position information of the object, positioning of the object to which the position information relates takes place and subsequently, object data are acquired by the acquisition unit, and are compared with the target position of the object. Preferably, the positioning of the object is carried out manually by the medical operating personnel. On the basis of the object data acquired, the position of the object can be continually monitored and/or checked during the preparation of the patient. In addition, every desired change of posture and/or change of position of the object can be communicated directly to the medical operating personnel. The target position of the object can be a target position of the patient and/or a target position of the accessory unit.

In another embodiment of the invention, a confirmation signal is emitted as an output, if the acquired object data matches the target position. The confirmation signal can be an optical and/or an acoustic confirmation signal, for example emission of a sound and/or a sound sequence and/or a display of a color change on the scanner unit and/or a flashing light, etc. The medical operating personnel thus can obtain a direct feedback for individual preparation steps during the preparation of the patient.

In another embodiment of the invention, the position information is projected anew if the acquired object data diverges from the target position. The medical operating personnel thus can obtain a direct feedback for individual preparation steps during the preparation of the patient.

The invention further concerns a medical imaging computer that is operated by a computer configured to cause the inventive method to be implemented. The medical imaging apparatus has a scanner, a patient positioning device for positioning the patient for a medical imaging investigation, an acquisition unit for the acquisition of patient data, a calculation computer for calculation of the position data, and a projection unit for projection of the position data.

The apparatus provides support for medical operating personnel during the preparation of a patient for a medical imaging investigation. Simple and time-saving assistance for positioning the patient and/or for arranging and/or positioning accessory units is provided for inexperienced or unpracticed medical operating personnel. Consequently, by the support for an optimized positioning of the patient and/or the accessory unit, a faulty positioning can be prevented and thus the image quality can be improved. Measurement repetitions due to faulty positioning thus can avoided.

The advantages of the medical imaging device according to the invention substantially correspond to the advantages of the method according to the invention, as described in detail above. Features, advantages and alternative embodiments mentioned above apply to the apparatus as well.

The present invention also encompasses a non-transitory, computer-readable data storage medium encoded with programming instructions that, when the storage medium is loaded into a computer or computer system of a magnetic resonance apparatus, cause the computer or computer system to operate the magnetic resonance apparatus, or the data acquisition scanner thereof, in order to implement any or all embodiments of the method according to the invention, as described above.

DESCRIPTION OF THE PREFERRED EMBODIMENTS

Figure 1:
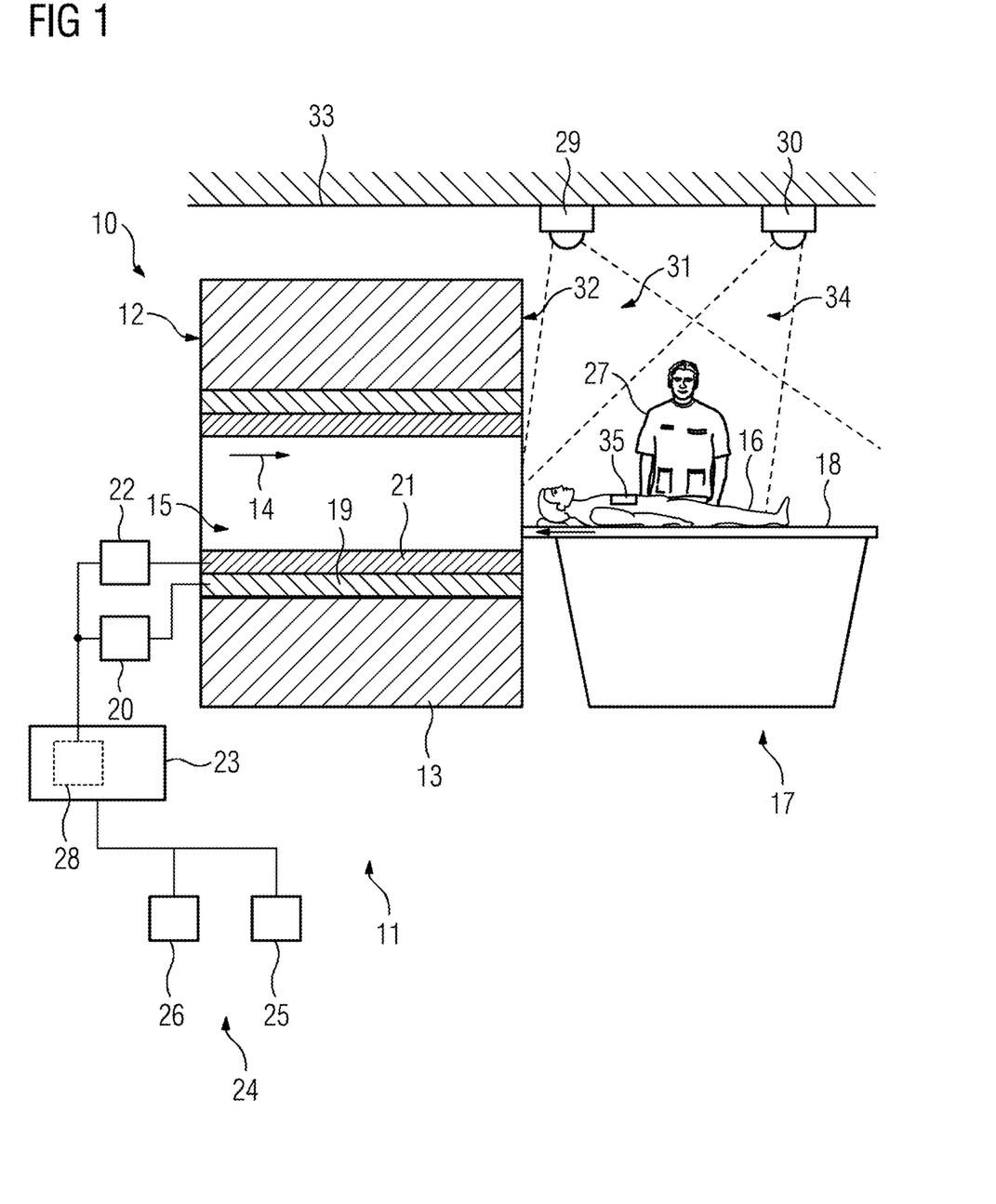
FIG. 1 is a schematically illustrates of a medical imaging apparatus according to the invention.

FIG. 1 schematically shows a medical imaging apparatus 10. In the exemplary embodiment, the medical imaging apparatus 10 is formed as a magnetic resonance apparatus 11, the present invention is described on the basis of the magnetic resonance example of the device 11. The present invention, however, is not restricted to the embodiment of the medical imaging apparatus 10 as a magnetic resonance apparatus 11 and further embodiments of the medical imaging apparatus 10 are readily conceivable, for example, a computed tomography device, a PET device, etc.

The magnetic resonance apparatus 11 has a scanner 12 that has a superconducting basic field magnet 13 for generating a strong and constant basic magnetic field 14. The scanner 12 has a patient receiving region 15 to accommodate a patient 16. In the present exemplary embodiment, the patient receiving region 15 is cylindrical and is surrounded cylindrically by the scanner 12. In principle, however, a configuration of the patient receiving region 15 deviating therefrom is readily conceivable. The patient 16 can be pushed and/or moved by a patient positioning device 17 of the magnetic resonance apparatus 11 into the patient receiving region 15. For this purpose, the patient positioning device 17 has a patient table 18 that is movable within the patient receiving region 15.

The scanner 12 also has a gradient coil unit 19 that generates magnetic field gradients that are used for spatially encoding the MR signals during an imaging procedure. The gradient coil unit 19 is controlled by a gradient controller 20 of the magnetic resonance apparatus 10. The scanner 11 further has a radio-frequency antenna unit 21. The radio-frequency antenna unit 21 is controlled by a radio-frequency (RF) antenna controller 22 of the magnetic resonance apparatus 11 so as to radiate radio-frequency magnetic resonance sequences into an examination space which is substantially formed by a patient receiving region 15 of the magnetic resonance apparatus 11. The radio-frequency magnetic resonance sequence gives certain nuclear spins in the patient 16 a magnetization that causes those nuclear spins to be deflected from the polarization produced by the basic magnetic field 14. As those excited nuclear spins relax and return to the steady state (equilibrium) position, they emit MR signals that are detected by the same radio-frequency antenna from which the excitation signals were emitted, or by a different radio-frequency antenna.

For operating the basic field magnet 13, the gradient controller 20 and the radio-frequency antenna controller 22, the magnetic resonance apparatus 11 has a control computer 23. The control computer 23 centrally controls the magnetic resonance apparatus 11, for example so as to execute a pre-determined imaging gradient echo sequence. Furthermore, the control computer 23 has an evaluation processor (not disclosed in detail) for evaluating medical image data that are acquired during the magnetic resonance investigation.

Furthermore, the magnetic resonance apparatus 11 has a user interface 24, which is connected to the system control computer 23. Control information such as imaging parameters, and reconstructed magnetic resonance images, can be displayed on a display unit 25, for example, on at least one monitor of the user interface 24, for medical operating personnel 27. In addition, the user interface 24 has an input unit 26 via which information and/or parameters can be entered by the medical operating personnel 27 during a scanning procedure.

Furthermore, the magnetic resonance apparatus 11 has a calculation computer 28, an acquisition unit 29 and a projection unit 30. The calculation computer 28, the acquisition unit 29 and the projection unit 30, collectively implement the inventive method for supporting preparation of the patient 16 for a medical imaging investigation. In the exemplary embodiment, a magnetic resonance investigation is carried out. The method for supporting a preparation of a patient 16 for a magnetic resonance investigation is automatically and/or autonomously implemented by the magnetic resonance apparatus 11, in particular, the calculation computer 28 together with the acquisition unit 29 and the projection unit 30. For this purpose, the calculation computer 28 has a processor (not separately shown). Furthermore, the calculation computer 28 also has suitable calculation programs and/or calculation software. The calculation programs and/or calculation software can be stored in a memory (not separately shown) of the calculation computer 28 and/or of the magnetic resonance apparatus 11.

The calculation programs and/or calculation software can also be deposited in an external memory, for example a cloud, and the calculation computer 28 can access the calculation programs and/or calculation software via a data network.

The calculation computer 28 can be integrated within the control computer 23. Alternatively or additionally, the calculation computer 28 can be configured as an independent unit.

The acquisition unit 29 is formed in the present exemplary embodiment by a camera, in particular a 2-D camera or a 3-D camera for acquisition of 2-D patient data or 3-D patient data. The acquisition unit 29 is arranged within an examination room in which the scanner 12 is also situated. The acquisition unit 29 is arranged within the examination room such that an acquisition region 31 of the acquisition unit 29, in particular the camera, covers a region within which the preparation of the patient 16 for the magnetic resonance investigation takes place.

This acquisition region 31 or this preparation region are preferably situated in front of the scanner 12 and thereby directly adjoin a front side 32 of the scanner 12. The acquisition region 29 also covers a location in which the patient positioning device 17 for the preparation of the patient 16 is situated.

The acquisition unit 29 can be arranged on the scanner 12, in particular on the front side 32 of the scanner 12. Particularly advantageously, the acquisition unit 29 is arranged on a wall or a room ceiling 33 of the examination room, so that an unchanged view onto the patient 16 or the patient positioning device 17 is ensured during the preparation of the patient 16 for the magnetic resonance investigation.

Alternatively, instead of a camera, the acquisition unit 29 can be or include a sensor that acquires the patient data. The sensor can be integrated within the patient positioning device 17, for example as one or more pressure sensors are integrated within a surface of the patient positioning device 17 on which the patient lies, so that, on the basis of a detected pressure distribution, a conclusion can be made regarding the posture and/or orientation and/or size and/or position of the patient 16. The sensor can be formed as one or more RF sensors that acquire the patient data, which are integrated within the patient positioning device 17, in particular within a positioning surface of the patient positioning device 17.

The projection unit 30 is also arranged within the examination room in which the scanner 12 is situated. The projection unit 30 is arranged within the examination room such that a projection region 33 of the projection unit 30 covers a region within which the preparation of the patient 16 for the magnetic resonance investigation takes place. This projection region 34 and the preparation region are preferably situated in front of the scanner 12 and thereby directly adjoin the front side 32 of the scanner 12. The projection region 34 also covers a location in which the patient positioning device 17 for the preparation of the patient 16 is situated.

The projection unit 30 can be arranged on the scanner 12, in particular on the front side 32 of the scanner 12. Particularly advantageously, the projection unit 30 is arranged on the wall or the room ceiling 33 of the examination room, so that an unchanged view onto the patient 16 or the patient positioning device 17 is always ensured during the preparation of the patient 16 for the magnetic resonance investigation.

Alternatively or additionally, the projection unit 30 can be or include an LED strip on the patient positioning device 17, in particular on the patient table 18. With such an LED strip, a region of the patient 16 can be marked that is to be provided with an accessory unit 35, for example, a local radio-frequency antenna unit. For example, the LED strip can illuminate a region that includes a knee of the patient 16, so that the required knee radio-frequency antenna unit can be selected for the medical operating personnel 27.

Figure 2:
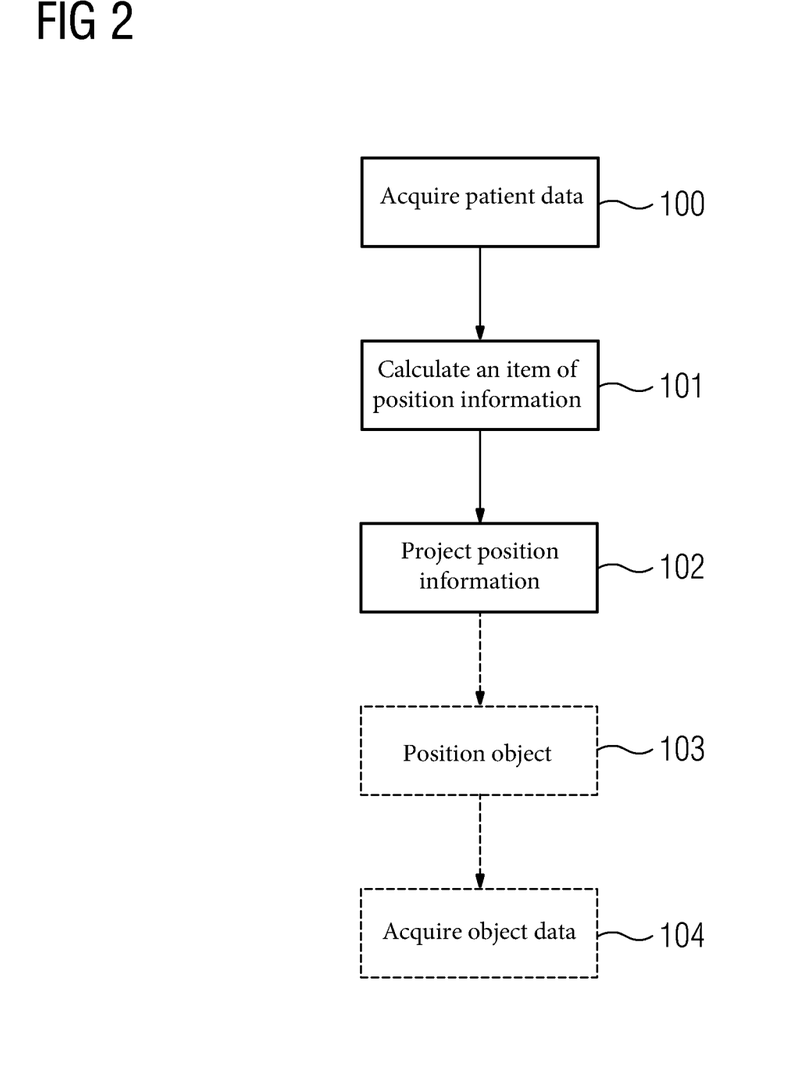
FIG. 2 is a flowchart of the inventive method for supporting a preparation of a patient for a medical imaging investigation.

The method for supporting medical operating personnel 27 during a preparation of a patient 16 for a medical imaging investigation, in particular a magnetic resonance device, is shown in FIG. 2. At the start of the method, the patient 16 is already positioned beside the patient positioning device 17 or is already positioned on the patient positioning device 17. In a first method step 100, an acquisition of patient data of a patient 16 positioned beside the patient positioning device 17 or of a patient 16 positioned on the patient positioning device 17 takes place by means of the acquisition unit 29.

The acquired patient data preferably designate position data of the patient 16. If the patient 16 is already positioned on the patient positioning device 17, the position data of the patient 16 can designate the position and/or the posture and/or the orientation of the patient 16 in relation to the patient positioning device 17. In addition, the position data can designate an extent of the patient 16, in particular the size and/or the length and/or the width and/or the height.

For easier acquisition of the position data, in addition, the patient 16 can be provided with landmarks. Preferably, a region of the patient 16 to be investigated is also provided with landmarks.

Subsequently, the acquired patient data are transferred from the acquisition unit 29 to the calculation computer 28 via a data transfer unit (not separately shown) of the magnetic resonance apparatus 11.

In a further method step 101, calculation of an item of position information of an object takes place by the calculation computer 28. The calculation takes place on the basis of the patient data and/or on the basis of an item of investigation information and/or on the basis of data from accessory units 35. The data of the accessory units 35 is preferably stored in a database (not separately shown) so that the calculation computer 28 can access the data of the accessory units 35 of the database by the data network. The data of the accessory units 35 typically designates a geometry, in particular the length and/or the width and/or the height of the individual accessory units 35, the data are stored together with the respective accessory units 35. Alternatively or additionally, the data of the accessory units 35 can designate a target position of the individual accessory units 35 in relation to the patient positioning device 17 and/or in relation to the patient 16, with the target position being stored together with the respective accessory units 35. In addition, the data of the individual accessory units 35 can designate a usage area, in particular for which type of investigations the individual accessory units 35 can be used. Such data are stored together with the respective accessory units 35. Preferably, all the accessory units 35 available on site are stored within the database.

The individual accessory units 35 can be, for example, local radio-frequency antenna units that are positioned for the magnetic resonance investigation around the region of the patient 16 to be investigated. The accessory units 35 can also be an ECG unit and/or a breathing sensor and/or other units considered useful by those skilled in the art.

On the basis of the acquired patient data, first, a body model of the patient 16 can be created (calculated) by the calculation computer 28. Preferably, for this purpose, the calculation computer 28 accesses a body model algorithm, with which the body model of the patient can be ascertained or determined on the basis of the acquired patient data.

The investigation information can include a clinical picture and/or an investigation region of the patient 16. The investigation information can already be stored in a patient database and so can be called autonomously by the calculation computer 28. It may also be that the investigation information is entered directly by the medical operating personnel 27 via the input unit 26, and is subsequently available to the calculation computer 28.

Preferably, an item of position information of an object is determined by the calculation computer 28 on the basis of the body model and the investigation information and the data from the accessory units 35. If the object is the patient 16, then the position of the patient 16 can be specified or checked. For example, first a position of the patient 16 on the patient positioning device 17 for the pending medical imaging investigation can be specified. Thereby, the position of the patient 16 can also designate the orientation of the patient 16 on the patient positioning device 17. Furthermore, in head investigations or knee investigations of the patient 16 in which the local radio-frequency antenna unit has a predetermined position relative to the patient positioning device 17, a target position of the patient 16 relative to the radio-frequency antenna unit can be determined and/or calculated. In addition, for accessory units 35 integrated into the patient positioning device 17, for example, integrated radio-frequency antenna units with an integrated breathing sensor and/or ECG unit, a target position of the patient 16 relative to the accessory unit 35, in particular relative to the radio-frequency antenna unit and/or the breathing sensor and/or the ECG unit can also be determined or calculated.

If the object is an accessory unit 35, in the method step 101, position information, in particular a target position of the accessory unit 35, can be determined or calculated. For example, the orientation and/or position of an accessory unit 35 configured as a radio-frequency antenna unit for the magnetic resonance investigation can be determined. In addition, the position of an accessory unit 35 configured as ECG electrodes can be determined.

In addition, on the basis of the acquired patient data and on the basis of the investigation information, in the method step 101, at least one of the multiple accessory units 35 available can be selected by the calculation computer 28. For example, an accessory unit 35 configured as a body coil can be selected on the basis of the size of the patient 16.

In a further method step 102, a projection of the position information of the object takes place by the projection unit 30. If the position information includes a target position of the patient 16, then the target position of the patient 16 is projected onto the patient positioning device 17 and/or the patient 16. The target position can thereby be marked by an illuminated area which marks the target position of the patient 16, and/or can be an outline and/or a periphery of the target position.

In addition, the target position can designate a change of position of the patient 16 that is projected onto the patient 16 and/or the patient positioning device 17. The change of position can be indicated, for example, by projected arrows.

Figure 3:
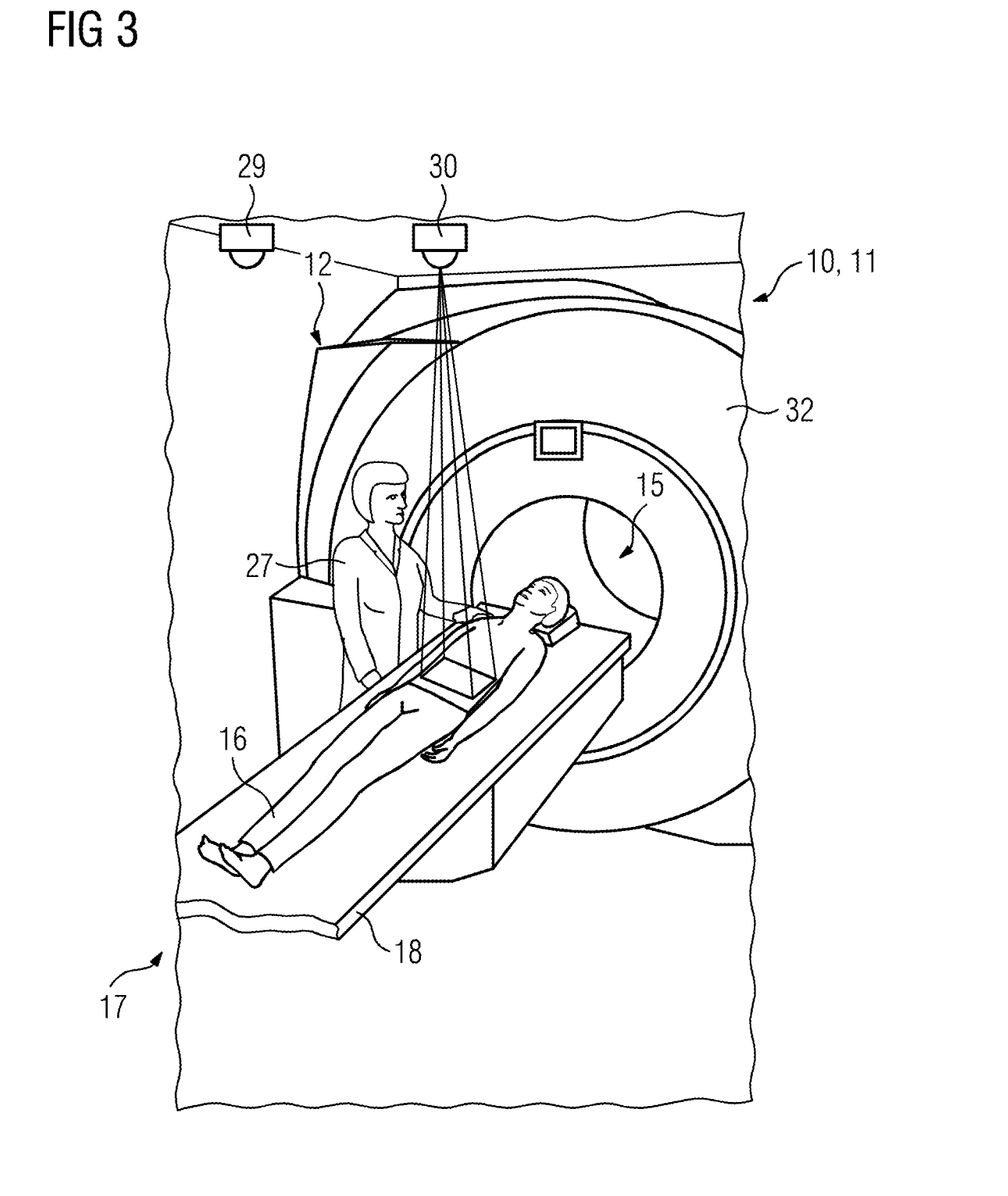
FIG. 3 shows an example of a projection of an item of position information on the patient in accordance with the invention.

If the position information of the object includes a target position of an accessory unit 35, this target position of the accessory unit 35 can also be projected onto the patient 16. For example, on the basis of a projected area and/or of a projected periphery, the target position of the accessory unit 35 can be indicated on the patient 16. Shown in FIG. 3 as an example is a projection of a target position of an accessory unit 35 on the patient 16 positioned on the patient positioning device 17.

Simultaneously with the projection of the target position of the object, an output can take place via a display on the scanner 12, for example, an output in text form.

In a further optional method step 103, following the projection of the position information of the object, a positioning of the object takes place. For example, the accessory unit 35 is positioned by the medical operating personnel 27 in the indicated or projected target position. Alternatively or additionally, the patient 16 can be positioned by the medical operating personnel 27 in the target position indicated and/or projected.

Subsequently in an optional further method step 104, an acquisition of object data takes place by the acquisition unit 29, whereby the acquired object data are compared by the calculation computer 28 with the target position of the object. For easier acquisition of object data, in particular object data of an accessory unit 35, this can also be provided for recognition by means of markers. If the acquired object data matches the target position of the object, an emission of a confirmation signal, for example an acoustic and/or optical confirmation signal, takes places. If, however, the acquired object data diverges from the target position of the object, the position information, in particular the target position of the object, is projected anew by the projection unit 30.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for supporting preparation of a patient for a medical imaging examination, comprising:

acquiring patient data from a patient using acquisition circuitry, the patient data identifying a current position of the patient;

in a calculation processor provided with said patient data, calculating position information that designates a change in position of the patient for the medical imaging examination with respect to a deviation between a target position of the patient with respect to at least one accessory and the current position of the patient with respect to the at least one accessory, the position information being calculated using (i) an item of examination information including a clinical image of the patient that is provided to said calculation processor that is relevant to said medical imaging examination, and (ii) accessory data relating to the at least one accessory;

in the calculation processor, calculating an examination region of the patient using the clinical image of the patient; and from a projection circuitry in communication with said calculation processor, projecting said change in position of the patient onto at least one of the patient or a patient position device on which the patient is positioned for said medical imaging examination at a location of the examination region at which said medical imaging examination is to be implemented.

2. The method as claimed in claim 1, comprising using a camera as said acquisition circuitry.

3. The method as claimed in claim 1, comprising arranging landmarks on the patient and acquiring said patient data so as to represent said landmarks.

4. The method as claimed in claim 1, comprising:
accessing said accessory data from a memory.

5. The method as claimed in claim 1, comprising, in said calculation processor, determining a body model of the patient using said patient data.

6. The method as claimed in claim 1, comprising:
selecting said at least one accessory from among a plurality of available accessories using the patient data.

7. The method as claimed in claim 1, comprising:
calculating said position information so as to designate a target position of said at least one accessory; and
projecting, with said projection circuitry, said target position of said at least one accessory onto the patient.

8. The method as claimed in claim 1, further comprising:
comparing the current position of the patient with the target position of the patient.

9. The method as claimed in claim 8, comprising emitting a confirmation signal when the current position of the patient matches said target position of the patient.

10. The method as claimed in claim 8, comprising repeating projecting said change in the position of the patient when the current position of the patient diverges from said target position of the patient.

11. The method as claimed in claim 1, wherein the acquisition circuitry comprises a sensor integrated within a patient positioning device that is used to position the patient for the examination, and
wherein the sensor is configured to generate the patient data indicative of the current position of the patient based upon a pressure distribution of the patient on the patient positioning device.

12. The method of claim 1, wherein the accessory comprises one of a local radio-frequency antenna accessory, an electrocardiogram (ECG) accessory, or a breathing sensor accessory.

13. The method of claim 1, wherein the accessory data designates a geometry of the at least one accessory.

14. The method of claim 1, wherein the calculation processor is configured to calculate the position information to be used in the medical imaging examination based on each of (i) the patient data, (ii) the item of examination information, and (iii) the accessory data.

15. The method of claim 1, wherein the position information further designates a target position of at least one accessory to be used in the medical imaging examination, and
wherein the projection circuitry is configured to project, as part of the position information, the target position of the at least one accessory at a location at which said medical imaging examination is to be implemented.

16. The method of claim 1, further comprising:
calculating, via the calculation processor, a body model of the patient using the acquired position information to determine the current position of the patient.

17. The method of claim 1, wherein the clinical image of the patient includes a description of anatomical locations of the patient identified with experienced symptoms.

18. A medical imaging apparatus comprising:
acquisition circuitry configured to acquire patient data from a patient using acquisition circuitry, the patient data identifying a current position of the patient;
a calculation processor provided with said patient data, and configured to calculate position information that designates a change in position of the patient for the medical imaging examination with respect to a deviation between a target position of the patient with respect to at least one accessory and the current position of the patient with respect to the at least one accessory, the position information being calculated using (i), an item of examination information including a clinical image of the patient that is provided to said calculation processor that is relevant to said medical imaging examination, and (ii) accessory data relating to the at least one accessory to be used in said medical imaging examination, wherein the calculation processor is further configured to calculate an examination region of the patient using the clinical image of the patient; and projection circuitry in communication with said calculation processor, the projection circuitry configured to project the change in position of the patient onto at least one of the patient or a patient position device on which the patient is positioned for said medical imaging examination at a location of the examination region at which said medical imaging examination to be implemented.

19. The medical imaging apparatus of claim 18, wherein the clinical image of the patient includes a description of anatomical locations of the patient identified with experienced symptoms.

20. A non-transitory, computer-readable data storage medium encoded with programming instructions, said storage medium being loaded into a computer of a medical imaging apparatus, and said programming instructions causing said computer to:

receive patient data acquired from a patient using acquisition circuitry, the patient data identifying a current position of the patient;

calculate position information that designates a change in position of the patient for the medical imaging examination with respect to a deviation between a target position of the patient with respect to at least one accessory and the current position of the patient with respect to the at least one accessory, the position information being calculated using (i) an item of examination information including a clinical image of the patient that is provided to said computer that is relevant to said medical imaging examination, and (ii) accessory data relating to the at least one accessory to be used in said medical imaging examination;

calculate an examination region of the patient using the clinical image of the patient; and operate projection circuitry in communication with said computer to project the change in position of the patient onto at least one of the patient or a patient position device on which the patient is positioned for said medical imaging examination at a location of the examination region at which said medical imaging examination is to be implemented.

21. The non-transitory, computer-readable data storage medium of claim 20, wherein the clinical image of the patient includes a description of anatomical locations of the patient identified with experienced symptoms.

* * * * *